United States Patent [19]

Berzofsky et al.

[11] Patent Number: 5,081,226

[45] Date of Patent: Jan. 14, 1992

[54] SYNTHETIC PEPTIDES SHARING SEQUENCE HOMOLOGY WITH THE HIV ENVELOPE PROTEIN

[75] Inventors: Jay A. Berzofsky; Charles DeLisi, both of Bethesda; Hanah Margalit, Rockville, all of Md.; James L. Cornette, Ames, Iowa; Kemp B. Cease, Rockville; Cecilia S. Ouyang, Silver Springs, both of Md.

[73] Assignee: The United States of America as represented by the Department of Health and Human Services, Washington, D.C.

[21] Appl. No.: 492,318

[22] Filed: Feb. 28, 1990

Related U.S. Application Data

[63] Continuation of Ser. No. 14,430, Feb. 12, 1987, abandoned, which is a continuation-in-part of Ser. No. 747,935, Dec. 30, 1986, abandoned.

[51] Int. Cl.⁵ ........................ C07K 7/08; A61K 37/18
[52] U.S. Cl. .................................... 530/324; 530/327; 530/326; 530/325; 530/350; 514/2; 514/8; 514/10; 514/14; 514/13; 514/12; 514/21; 424/88
[58] Field of Search ............... 530/350, 324, 206, 324, 530/325, 326, 327, 328, 329; 514/12, 13, 14, 15, 16, 21, 8; 424/88

[56] References Cited

U.S. PATENT DOCUMENTS

| | | | |
|---|---|---|---|
| 4,525,300 | 6/1985 | Koshida et al. | 530/326 |
| 4,554,101 | 11/1985 | Hopp | 514/12 |
| 4,629,783 | 12/1986 | Cosand | 530/326 |
| 4,663,436 | 5/1987 | Elder et al. | 424/88 |
| 4,689,398 | 8/1987 | Wu et al. | 530/327 |

OTHER PUBLICATIONS

Chang et al., Bio/Tech., 3, 905-9, (1985 Oct.).
Pauletti et al., Anal Bioch., 151, 540-6, (1985).
Modrow et al., J. Virol., 61(2), 570-8, (Feb. 1987).
Allan et al., Science, 228, 1091-5, (1985).
Baum, Chem. Eng. News, 65(47), 14-34, (Nov. 1987).
Ratner et al., Nature, 313, 277-84, Jan. (1985).
Wain-Hobson et al., Cell, 40, 9-17, (1985).
Lasky et al., Science, 233, 209-12, (Jul. 1986).
Veronese et al., Science, 229, 1402-5, (1985 Sep.).
Weigant et al., Bioch. Biophys. Res. Comm., 139(1), 367-74, (Aug. 1986).
Chanhb et al., Eur. J. Immunol., 16, 1465-8, 1986.
Pert et al., P. N. A. S (U.S.A.), 83, 9354-8, (Dec. 1986).
Wang et al., PNAS(U.S.A.), 83, 6159-63, (Aug. 1986).
Willey et al., PNAS, 83, 5038-42, (Jul. 1986).
Cabradilla et al., Bio/Technology, 4, 128-33 (Feb. 1986).
Clerici, et al., "Interleukin-2 production used to detect antigenic peptide recognition by T-Helper lymphocytes from asymptomatic HIV-seropositive individuals"; Nature, vol. 339, No. 6223, pp. 383-385, 1st Jul. 1989.
Hale, et al., "T cell multideterminant regions in the human immunodeficiency virus envelope: toward overcoming the problem of major histocompatibility complex restriction", Inter. Immunol., vol. 1, No. 4, pp. 409-415, May. 1989.
Hosmalin, et al., Manuscript, "Priming with Helper T-Cell Epitope Peptides Enhances the Antibody Response to the Envelope Glycoprotein of HIV 1 in Primates", pp. 1-29.
Margalit, et al., J. Immunol., vol. 138, No. 7, "Prediction of Immunodominant Helper T Cell Antigenic Sites from the Primary Sequence", Apr. 1, 1987, pp. 2213-229.,

*Primary Examiner*—Esther L. Kepplinger
*Assistant Examiner*—Jeff Kushan
*Attorney, Agent, or Firm*—Mishrilal Jain

[57] ABSTRACT

This invention relates to the identification of short peptide segments of AIDS virus proteins which elicit T cellular immunity, and to a method of inducing cellular immunity to native proteins of the AIDS virus by immunization with short synthetic peptides. Five potential peptides have been identified by searching for regions which can fold as a maximally amphipathic helix. These may be useful to include in either a synthetic peptide- or recombinant fragment- based vaccine.

5 Claims, 5 Drawing Sheets

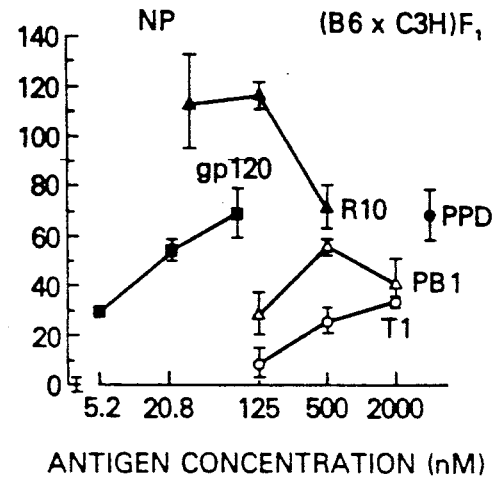
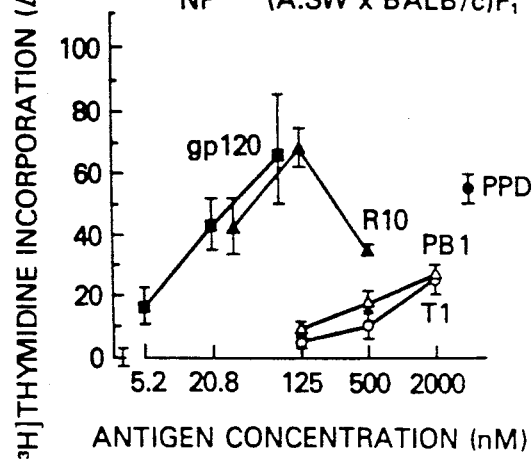
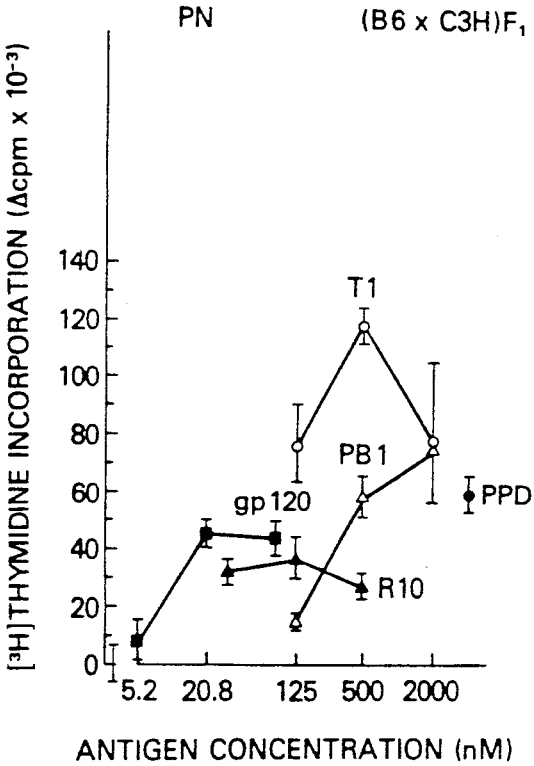
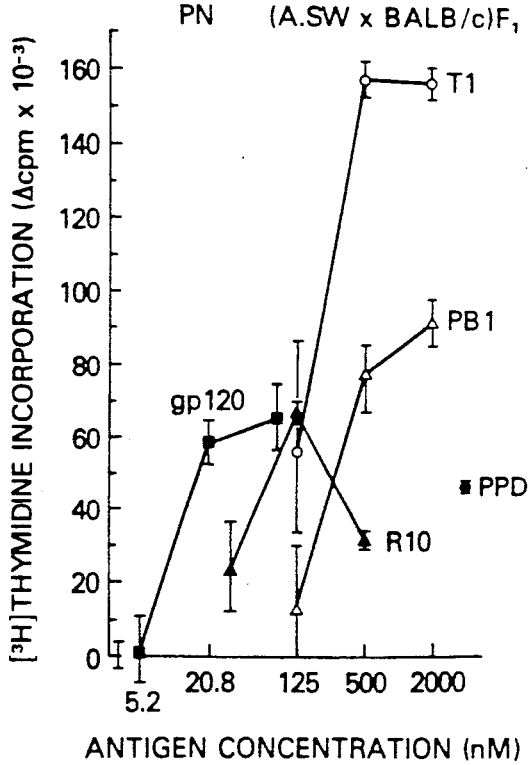

SYNTHETIC PEPTIDES SHARING SEQUENCE HOMOLOGY WITH THE HIV ENVELOPE PROTEIN

CROSS-REFERENCE TO RELATED APPLICATIONS

This application is a continuation of application Ser. No. 07/014,430 filed Feb. 12, 1987, now abandoned, which in turn is a continuation in part of Ser. No. 747,935 filed Dec. 30, 1986, now abandoned, with the same title and inventors.

The purpose of the present invention is to develop a vaccine to prevent acquired immunodeficiency syndrome (AIDS) based partly or solely on synthetic peptides which produce T cell immunity. T cell immunity is an important arm of defense against viral infections, but has hardly been studied for AIDS. Helper T cells are needed for an antibody response as well as for a cytotoxic T cell response and for inducing macrophage and LAK cell killing. While it is not yet clear whether cellular immunity or humoral immunity is the critical element in protection against a virus, the peptides of the present invention are particularly suited for use in a vaccine capable of safely eliciting either type of immunity: (1) the peptides are synthetically produced, and therefore do not include live virus, or a part of a live virus, or other sites which might produce deleterious effects (e.g., the site binding to T4 or the site producing cell fusion); (2) the peptides may be used alone to induce cellular immunity; (3) the peptides may be used in conjunction with other molecules in order to induce antibody production or a humoral response; and (4) the peptides may be targeted for a particular type of T-cell response without the side effects of other unwanted responses.

BACKGROUND OF THE INVENTION

Much effort has been devoted to the analysis of antibodies to AIDS virus antigens, but no previous studies have defined antigenic sites of this virus which elicit T cell immunity, even though such immunity is important in protection against many other viruses. Analysis of immunodominant helper T cell cell sites has suggested that such sites tend to form amphipathic helices. Using an algorithm based on this model, two candidate T cell sites, env T1 and env T2, were identified in the human T cell lymphotropic virus type IIIb (HTLVIIIb) envelope protein that were conserved in other Human Immunodeficiency Virus (HIV) isolates. Corresponding peptides were synthesized and studied in genetically defined inbred and F$_1$ mice for induction of lymph node proliferation. After immunization with a 425 residue recombinant envelope protein fragment, significant responses to native gp120 as well as to each peptide were observed in both F$_1$ combinations studied. Conversely, immunization with env T1 peptide induced T cell immunity to the native gp120 envelope protein. The genetics of the response to env T1 peptide were further examined and revealed a significant response in three of four independent Major Histocompatibility haplotypes tested, an indication of high frequency responsiveness in the population.

Identification of helper T cell sites should facilitate development of a highly immunogenic, carrier-free vaccine that induces both T cell and B cell immunity. The ability to elicit T cell immunity to the native AIDS viral protein by immunization with a 16-residue peptide suggests that such sites represent potentially important components of an effective AIDS vaccine.

Since the discovery of the human immunodeficiency viruses, the causative agents of the acquired immunodeficiency syndrome (AIDS), substantial progress has been made toward characterizing the viral genes and their products in infected cells. Though responsible for profound immunodeficiency, viral infection in man consistently induces a detectable immune response as evidenced by serum antibodies to the major viral proteins. Studies of serum reactivity to specific viral proteins have revealed no consistent prognostic associations to date. Much of the host antibody response is focused on the envelope proteins gp120 and gp41 (see FIG. 1). The ability of native gp120 or a large recombinant fragment to induce neutralizing antibodies has been demonstrated. Two apparently immundominant antibody binding sites in the gp41 envelope protein have been defined at the level of small synthetic peptides. Though such antibody sites are clearly of diagnostic importance and potentially of importance for vaccine design, the typical progression of AIDS in patients despite the presence of these antibodies suggests that effective T cell immunity is important to the immune defense against this pathogen.

An ideal vaccine is highly immunogenic, induces both T cell and B cell virus-specific immunity, and is free of irrelevant carrier proteins. While traditional approaches using whole virion or virion subunits can generally achieve this, practical considerations such as safety and availability of native antigen have led many to consider more highly engineered vaccine constructs for AIDS. Localization of immunodominant T cell and B cell recognition sites becomes critical if one wishes to design a vaccine based on recombinant proteins or synthetic peptides. A T cell response to the gp120 envelope protein has been demonstrated recently by Zarling et al. *Nature*, 323: 344-345 (1986) in macaques immunized with vaccinia constructs containing gp120 coding sequence. However, identification and characterization of immunodominant T cell sites within this 518 residue protein or other HIV proteins have not been reported.

Antibodies typically recognize free antigen in native conformation and can potentially see almost any site exposed on the antigen surface. In contrast, typical CD4+ helper T cells recognize antigen only in the context of the class II major histocompatibility (MHC) molecule and only after appropriate antigen processing usually consisting of proteolysis or denaturation. Additionally, the polyclonal T cell response is focused only on relatively few discrete sites. This limited response is seen even for non-eukaryotic proteins (e.g., influenza hemagglutinin and staphylococcal nuclease) for which tolerance to homologous host proteins does not limit the number of antigenic sites. Therefore, it is important to find sites which do elicit T-cell immunity to AIDS viral proteins. The elucidation of features determining immunodominance residing both intrinsic and extrinsic to antigen is the focus of much current basic and clinical interest. Detailed characterization of immunodominant T cell sites has allowed exploration for general features. Such analysis led to the observation that immunodominant T cell sites tend to have an amino acid sequence consistent with formation of an amphipathic helix with hydrophilic residues on one face and hydrophobic residues on the opposite face. In an amphipathic alpha helix, the hydrophobicity varies sinusoidally with a period of 3.6 residues per turn of the helix or a frequency of 100° per residue. An amphipathic $3_{10}$ helix has a period of 3 and a frequency of 120°. Based on this model, an algorithm entitled AMPHI, has been developed for identification of such sequences in proteins given only primary sequence data.

Although Zarling et al., *Nature* 323: 344 (1986), showed that T cell immunity to the AIDS virus envelope could be induced in monkeys using a recombinant vaccinia virus carrying the gene for the whole envelope protein, their study did not identify antigenic sites stimulating these T cells. Also, vaccinia immunization has been discontinued in the U.S. because of danger of disseminated vaccinia infection and other side effects. A synthetic peptide vaccine would not carry any of these risks. Since it would be synthetic, there would be no risk of live AIDS virus contamination as might occur with a killed virus vaccine. A synthetic peptide which does not contain sites responsible for syncytia formation might produce fewer side effects than a large recombinant envelope protein containing such sites.

DESCRIPTION OF THE FIGURES

FIGS. 3A–3D show lymph node proliferation assays of HTLVIII envelope gp120 and related recombinant and synthetic peptide antigens. $F_1$ hybrid mice were immunized with either 10 micrograms of the large recombinant protein R10 (panels A and B labeled NP) or 3 nanomoles of peptide env T1 (panels C and D labeled PN) in 50 microliters of complete Freund's adjuvant (DIFCO, Detroit, Mich.) at the base of the tail. Eight days later the draining inguinal and periaortic lymph nodes were removed and a single cell suspension prepared. Assays were set up in quadruplicate with appropriate antigen in 96-well plates with $3 \times 10^5$ cells per well in complete medium consisting of RPMI 1640 with 44% Eagle's-Hanks' amino acid medium, 10% fetal bovine serum, $5 \times 10^{-5}$M 2-mercaptoethanol, 2 mM fresh-frozen L-glutamine (Gibco, Grand Island, N.Y.), 100 U/ml penicillin, and 100 micrograms/ml streptomycin (Gibco). Plates were incubated for 4 days at 37° in a 5% $CO_2$ incubator, pulsed with 1 microCi of [$^3$H]-thymidine (New England Nuclear, Boston Mass.) and harvested 18 hours later onto glass fiber paper. Thymidine incorporation into DNA was then quantitated by liquid scintillation counting.

The geometric mean and standard error of the mean for each group were determined and the no antigen background subtracted to obtain the delta cpm. The no antigen backgrounds were: A 21,771: B 17,844: C 30,674: D 29,298. The confidence intervals for the background values are shown at the zero position of each vertical axis (n=8). The panels are scaled according to the magnitude of the PPD positive control response.

FIGS. 4A–4D show the response of env T1 peptide immune lymph node cells to gp120 and related antigens in the independent parental mouse strains. C57BL/6, C3H/HeJ, A.SW, and BALB/c mice were immunized with the 16-residue env T1 peptide and lymph node proliferation assays were performed as described in the legend to FIG. 3. SW102 is a peptide representing sperm whale myoglobin residues 102–118. The no antigen (0) and PPD negative and positive controls are shown in the first position of each panel. The panels are scaled according to the magnitude of the PPD response. The no antigen backgrounds were: B6 16,334; C3H 74,253; A.SW 28,771; BALB/c 34,600.

Figure 5B:
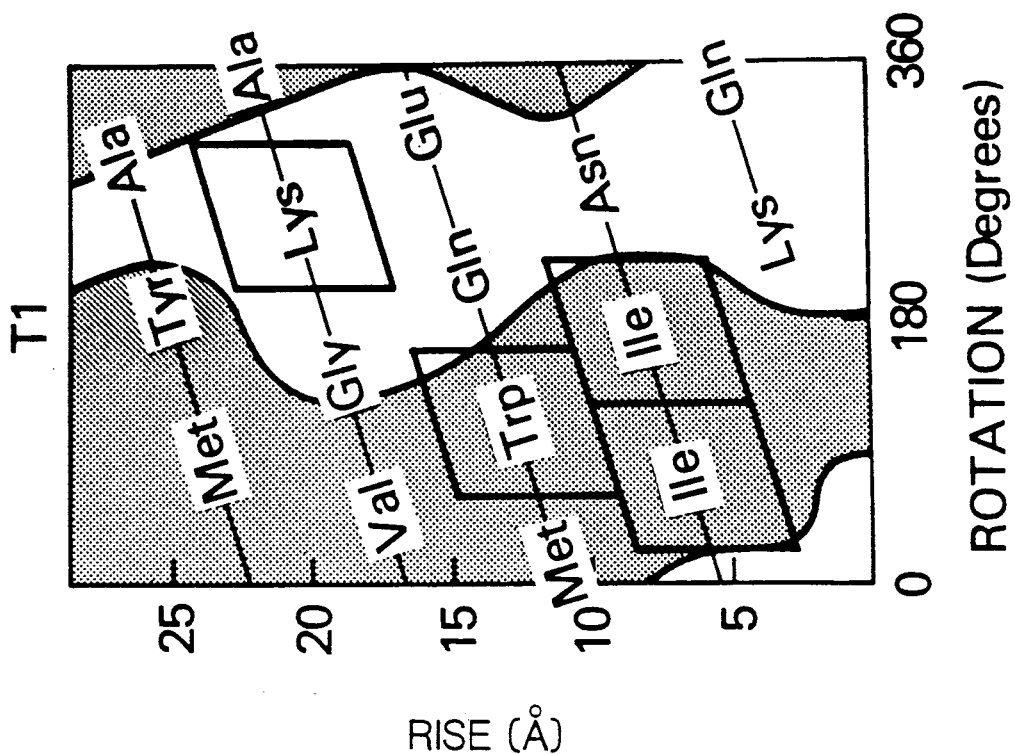
Figure 5A:
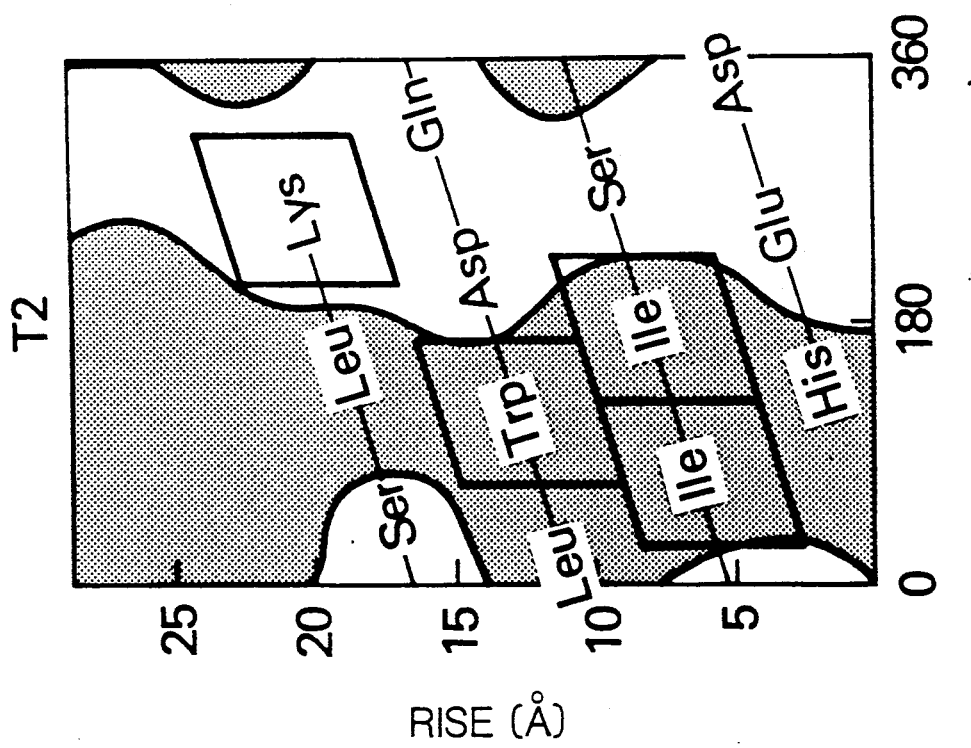

FIGS. 5A and 5B show alpha helical net representation of the env T2 and env T1 sites. This display can be thought of as slicing the cylinder of the helix lengthwise down one face, opening and flattening it. There are 3.6 residues per turn of the helix. The hydrophobic residues are shaded. Residues common to both sites are boxed. Regions outside of the peptides are shaded according to hydrophobicities of residues in the gp120 sequence.

UTILITY STATEMENT

Prediction of T-cell antigenic peptides has important implications for the development of artificial vaccines. Such vaccines are particularly useful in diseases like leprosy, caused by organisms which are hard to culture and for which the cellular arm of the immune system is the principal defense. Even when antibody production is the primary goal of vaccination, a secondary or anamnestic response requires the induction of helper T-cell immunity. Prediction of peptides for use as vaccines requires discovery and confirmation of properties correlating with T-cell antigenicity. One of the purposes of this invention is to use such properties in a process capable of reliably predicting T-cell stimulation by a protein segment.

T-cell immunity is not only important in the defense against many viral infections; T-cell help is also necessary for a memory antibody response. However, only a limited number of segments of protein antigens elicit T-cell immunity. None have previously been found for any proteins of the AIDS virus. The T-cell antigenic sites from AIDS viral proteins covered by the present invention should be very useful in any vaccine developed for this virus. The present invention also shows that one of the peptides elicits T-cell immunity to the native AIDS gp120 envelope protein. Thus, these peptides may constitute all or part of a synthetic vaccine. Also, a fragment vaccine made by recombinant DNA or other technology should be designed to include these sites.

DEFINITIONS

Definitions used in the present invention are as follows: the experimental peptides containing the immunodominant sites are defined as antigenic sites. "Antigenicity" in this invention always refers to T-cell antigenicity.

In vivo, an antigenic protein probably passes through three main steps before raising a helper T-cell response: (a) "processing": an antigen-presenting cell (APC), usually a macrophage, dendritic or B cell, ingests the protein and then digests it into smaller peptides; (b) "presentation": these peptides are then presented to T-cells, probably in conjunction with a Class II Major Histocompatibility Complex Protein on the APC surface; and (c) "recognition": a helper T-cell receptor then recognizes some combination of peptide and Class II Protein, and initiates a T-cell response.

Two antigenic properties are thought to contribute to this process, amphipathicity and Alpha-helicity, based on the findings in this invention.

A structure is amphipathic when it has both a hydrophobic portion and a hydrophilic portion. A peptide is segmentally amphipathic when the peptide contains at least two disjoint subpeptides, one hydrophobic, the other side hydrophilic. A peptide is alpha-amphipathic if, when the peptide is put into an alpha-helical conformation, one side of the alpha-helix is hydrophobic, the other side hydrophilic. A peptide is helically amphipathic if, when put into an alpha or $3_{10}$ helix, or similar helical structure, one side of the helix is hydrophobic and the other side hydrophilic. Both segmental amphipathicity and helical-amphipathicity are believed to contribute to T-cell antigenicity, though opinions about their relative importance differ.

SUMMARY OF THE INVENTION

The present disclosure is a method of inducing cellular immunity to native proteins of the AIDS virus by immunization with short synthetic peptides. Five potential peptides are identified by searching for regions which can fold as a maximally amphipathic helix. Two of these are recognized by T cells immune to the AIDS virus envelope protein. One of these was used to immunize mice and can successfully induce T cell immunity to the whole AIDS envelope protein (480 amino acid residues long) using this 16-residue peptide in 3 of 4 mouse strains tested. The invention includes but is not limited to these specific peptides and any synthetic peptides containing or overlapping these sequences or variations therein, including peptides with amino acid substitutions that retain or enhance the activity documented. These can be used alone as a vaccine or in combination with other materials (e.g. primary immunization with peptide, boost with recombinant fragment). They can also be attached to sites binding neutralizing antibodies to induce a neutralizing antibody response.

The present invention is critical to the manufacture of peptide vaccines capable of eliciting T-cell immunity. One aspect of the present invention is the discovery of certain traits which seem to be common to most T-cell stimulating protein segments. Such peptide vaccines should optimally be those protein segments which (a) have a propensity to form amphipathic alpha-helices; (b) do not have regions with a propensity to coil formations, and (c) have a lysine at their COOH-terminus. The last two observations are of particular use in manufacturing peptides vaccines: they indicate where the synthetic peptides should be terminated.

SPECIFIC DISCLOSURE

In this study AMPHI was used to analyze the gp120 envelope protein of the HTLV IIIb isolates of HIV for sequences consistent with formation of amphipathic helices as potential T cell sites. Sites were ranked according to the apparent strength of helical amphipathicity as reflected in the Amphipathic Score and frequencies were examined for consistency. Sites were further selected for occurrence in constant regions of gp120 (based on a comparison of the sequence of six isolates) and for absence of N-linked glycosylation sites. AMPHI parameters for the two most favorable sites are shown in FIG. 2. Candidate T cell sites were selected by including appropriate flanking residues. Candidate T cell sites env T1 and env T2 were defined as residues 428 through 443 and 112 through 124, respectively. The standard epitope nomenclature employed consists of viral isolate, protein designation, site type, and assigned number or residue number (e.g. HTLVIII (bH10)env T1).

Synthetic peptides corresponding to these sites were prepared by solid phase peptide synthesis. Peptides were synthesized using standard methods of solid phase peptide peptide synthesis on a Vega 250 peptide synthesizer using double dicyclohexylcarbodiimide mediated couplings. HOBT preactivation couplings were performed when coupling Gln or Asn. The standard t-boc/benzyl amino acid protection strategy was employed with side chain protection of the following amino acids: Asp(O-benzyl), Glu(O-benzyl), His(tosyl), Lys(2-chlorobenzyloxycarbonyl), Ser(benzyl), Trp(formly), Tyr(2,6-dichlorobenzyl). The extent of coupling was monitored using the qualitative ninhydrin test and recoupling performed when less than 99.4% coupling was observed. Peptides were cleaved from the resin using the low/high hydrogen fluoride (HF) method [J. P. Tam, W. F. Heath, and R. B. Merrifield, *J. Am. Chem. Soc.* 105, 6442 (1983)]. For peptide env T2 standard HF cleavage was employed as removal of the tryptophan formyl protecting group was found not to be required for antigenic activity. Peptides were purified to homogeneity by gel filtration on Biogel P4 in 9% formic acid followed by reverse phase HPLC as described previously. Composition was confirmed and concentration determined by amino acid analysis (kindly performed by Robert Boykins). Native gp120 was purified by selective detergent extraction and immunoaffinity chromatography followed by dialysis. The recombinant proteins R10 and PB1 were produced by cloning restriction fragments KpnI(5923) to Bgl II(7197) or Pvu II(6659) to Bgl II(7197) from the BH10 clone of HTLVIIIb into the Repligen Expression Vector (REV) followed by expression in *E. coli* and purification. Protein R10 contains residues 49 through 474 and PB1 residues 294 through 474 of the envelope protein.

As a genetically defined model of an outbred population, there was studied the immune response to these proteins in (C57BL/6×C3H/HeJ)$F_1$ and (A.SW x BALB/c)$F_1$ mice (H-$2^{bxk}$ and H-$2^{sxd}$ respectively). This strategy provides for full H-2 expression and complementation in the context of four different strain backgrounds. T cells have been shown to be responsible for the proliferation observed in antigen specific lymph node proliferation assays and consequently such assays were employed as a measure of T cell immunity.

Quantities of purified gp120 available precluded use in immunization and thus the R10 protein containing the majority of the gp120 sequence in nonglycosylated form was the largest immunogen used. FIG. 3 panels A and B shows the lymph node proliferative response of R10 immune mice tested with native gp120, recombinant proteins, and synthetic peptide env T1. In both $F_1$ hybrids a strong response was observed not only to the immunogen R10, but also to gp120. Therefore, the response was largely directed at envelope sequence and not at the irrelevant vector-derived flanking sequence encoded residues in the recombinant protein. Thus the recombinant R10-fragment is an effective immunogen for priming for a response to the native gp120. The response to the synthetic peptide env T1 indicates that a significant component of the T cell response to the 425 residue R10 is in fact focused on the 16 residue env T1 site. In other experiments with R10 immune lymph node cells a response to peptide env T2 similar to that to peptide env T1 was observed (table I).

Given that immunization with a large fragment spanning most of the gp120 sequence elicits a response partially focused on a small site defined by a synthetic peptide (a native immunogen/peptide test-antigen or NP experiment), we next asked whether immunization with the synthetic peptide would elicit immunity to the native protein (a peptide immunogen/native test-antigen or PN experiment). Immunogenicity in the PN direction would appear to be a prerequisite for efficacy as a vaccine site. The results of such an experiment in the F1 mice is shown in FIG. 3 panels C and D. Mice immunized with env T1 peptide showed substantial immunity not only to the env T1 immunogen but also to the native gp120 as well as to the recombinant proteins. Thus a 16-residue synthetic peptide selected on the basis of amphipathicity can elicit T cell immunity to the native AIDS virus protein.

To further characterize genetic restriction of the response to env T1 there was studied the independent H-2 disparate parental strains from which the $F_1$ hybrids have been derived; C57BL/6, C3H/HeJ, A.SW and BALB/c. Mice were immunized with env T1 peptide and studied with native and peptide antigens. As shown in FIG. 4, C57BL/6 ($H-2^b$ haplotype) was found be a low responder, whereas the other strains ($H-2^k$, $H-2^s$, and $H-2^d$ haplotypes) were intermediate or high responders to the env T1 peptide. The response to native gp120 paralleled that to the peptide. A corresponding pattern of responsiveness is also observed in experiments using H-2 congenic strains of mice (table II). Thus peptide env T1 represents a 16-residue peptide that can prime T cells for a secondary response to the 518 residue glycosylated native gp120 in multiple MHC haplotypes.

An unexpected finding was the striking cross reaction between env T1 and env T2 peptides. The env T1 immune cells responded to env T2 as well as to the immunizing peptide. Cross reactivity of env T2 was most pronounced on the $H-2^k$ haplotype. Prompted by this finding, the two sequences were compared and there was a degree of homology which was even more evident when considered in the context of possible alpha helical structure as shown in FIG. 5. Not only do env T1 and env T2 share the hydrophobic Ile-Ile-Xxx-Yyy-Trp cluster on the hydrophobic face and the Lys on the hydrophilic face of the helix, but also the spatial relationship between these is identical. Gln and acidic amino acids (Glu, Asp) neighboring the Lys are observed in both cases as well. The poor reactivity to peptide 102-118 of sperm whale myoglobin which is derived from an unrelated protein and shares minimal homology with env T1 indicates that the property of being an amphipathic alpha-helical peptide is not sufficient for cross-reactivity. As an additional specificity control gp120, env T1 and env T2 were tested using lymph node cells immune to an unrelated antigen, sperm whale myoglobin, and were found to be non-stimulatory (data not shown).

Though species differences are certain to influence the T cell repertoire, the molecules and mechanisms leading to a T cell response are conserved across species and thus the factors determining immundominance are similar as well. The one helper T cell site (from influenza virus) that has been characterized at the synthetic peptide level in man is in fact immunodominant in mice as well and has an amino acid sequence consistent with formation of a highly amphipathic alpha helix.

Figure 1:
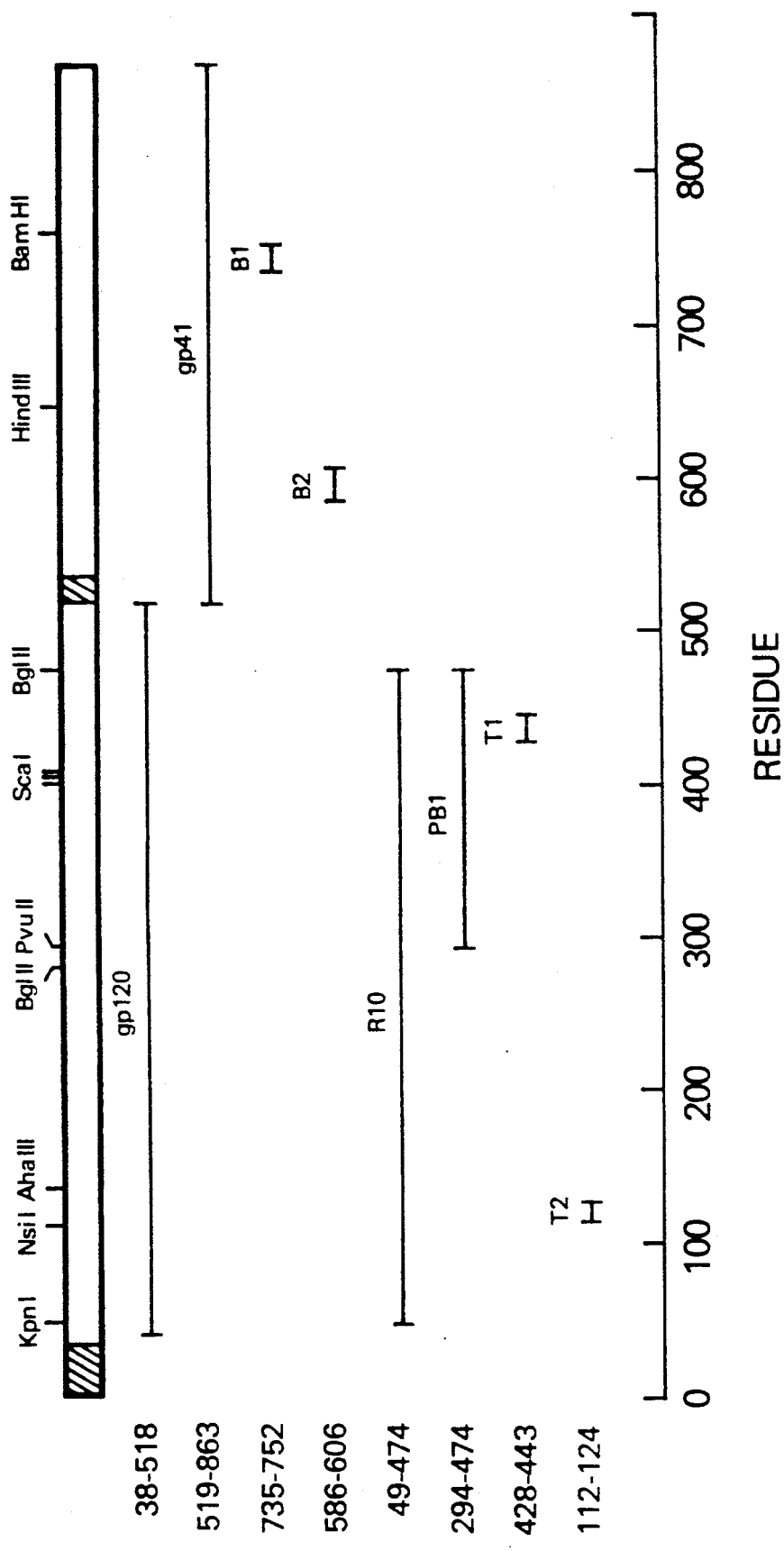
FIG. 1 shows the HTLVIII gp160 envelope protein. The gp120 and gp41 proteins are shown along with recombinant proteins and synthetic peptides referred to in this study. Selected restriction site locations are shown on the map at the top along with the shaded leader peptide (1–37) and transmembrane region (519–534). The precursor gp160 is cleaved to form the gp120 and gp41 proteins. The dimensions and locations of the R10 and PB1 recombinant proteins and the env T1 and T2 synthetic peptides examined in this study are shown. The locations of known B cell epitopes (B1 and B2) in the gp41 protein are also shown.
Figure 2A:
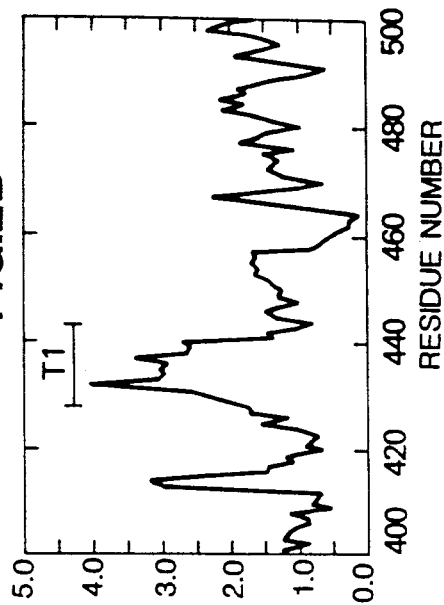
FIGS. 2A–2D show the results of AMPHI analysis in the region of the env T1 and env T2 sites.
Figure 2B:
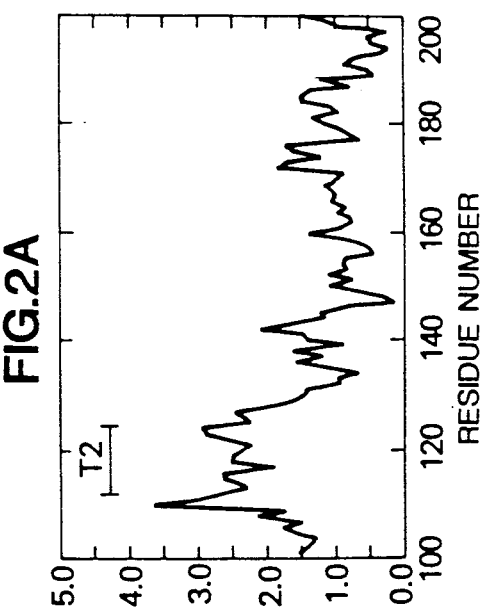
Figure 2C:
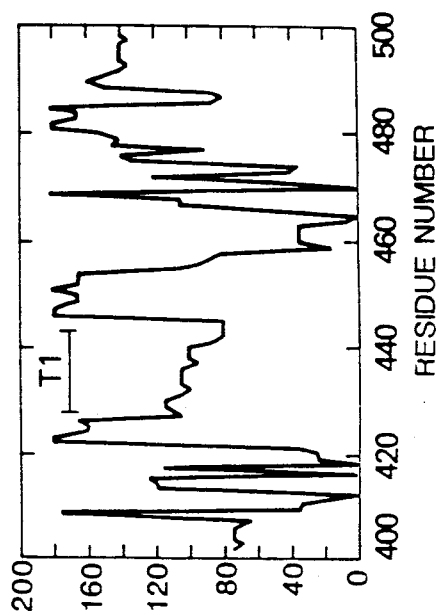
Figure 2D:
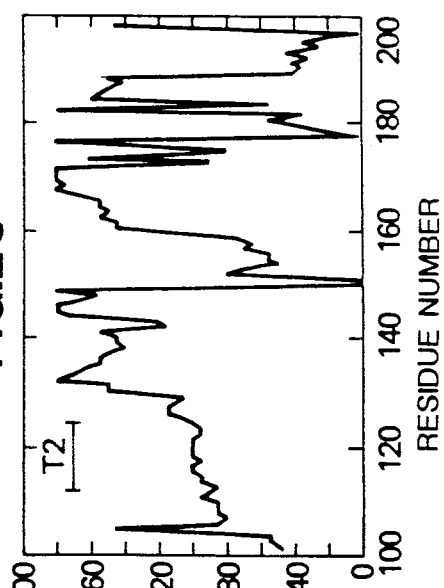
Figure 4A:
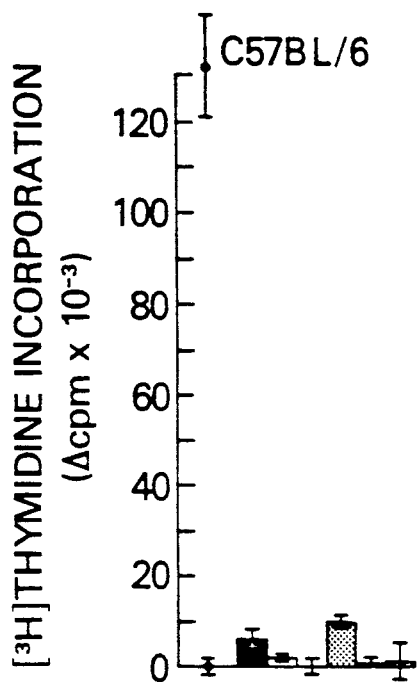
Figure 4B:
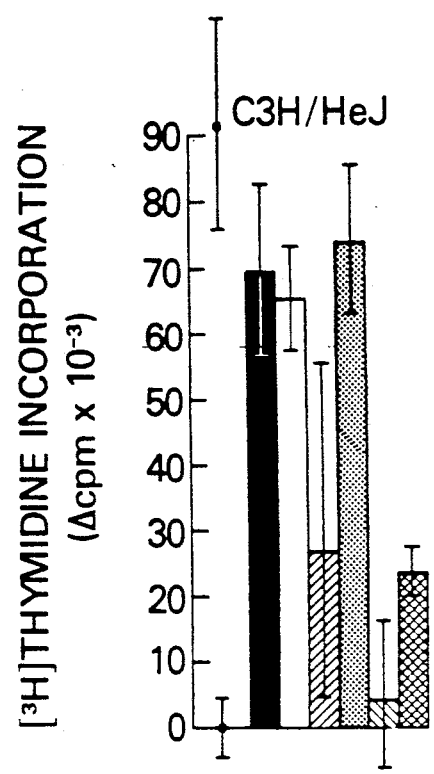
Figure 4C:
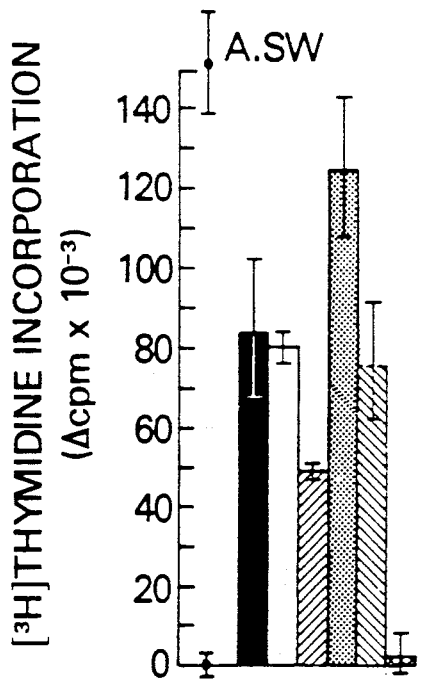
Figure 4D:
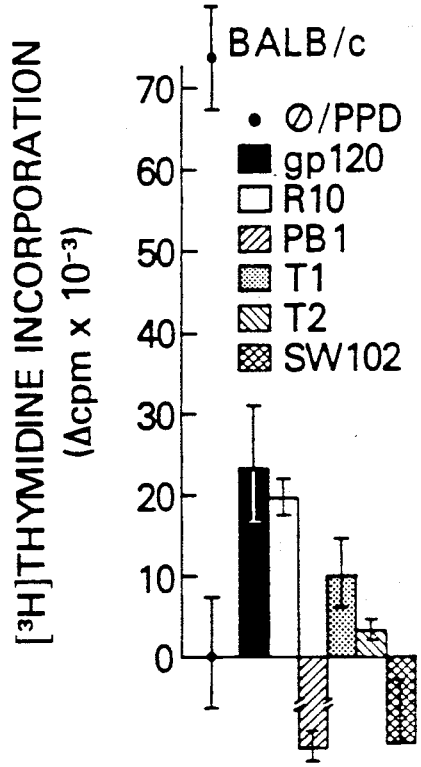

Analysis of the various viral proteins in the thirteen HIV isolate sequences published shows the envelope gene to be the most variable. Such analysis reveals discrete variable and conserved regions. A polyvalent vaccine might thus appropriate. Both the env T1 and the env T2 sites are highly conserved in the HIV sequences reported to date. The env T2 site is the more highly conserved of the two sites especially in the $LAV_{ELI}$ isolate. The previously described B cell sites (B1 and B2 in FIG. 1) fall within conserved regions as well.

Induction of T cell immunity may contribute in several ways to protection against HIV infection. Though AIDS progresses despite the presence of detectable antibody to viral proteins in most patients, low titer neutralizing antibody has been demonstrated in many such patients. Neutralizing titers are substantially higher in healthy AIDS related complex patients and in HIV antibody positive hemophiliacs. Whether this relationship is causal or simply correlative is as yet unknown. If these or any other antibodies are in fact protective, provision of optimum T cell help at the time of immunization as well as when faced with an infectious challenge would appear essential. Substantial T cell help should also be required for an effective cell mediated response to infected cells. NK cells have been shown to selectively kill HIV infected cells in vitro. Given that a major mode of viral transmission in the infected patient is thought to be cell to cell, a vaccine that primes helper T cells for augmentation of NK cell and possibly lymphokine activated killer cell activity is essential for an effective vaccine. Induction of virus-specific cytotoxic T lymphocyte (CTL) immunity which also requires helper T cells, is also desirable. While in some cases the determinants recognized by CTL can in fact be defined by small peptides, in vivo expression of antigens such as in a vaccinia or adenoviral vector may be required for efficient elicitation of a classical CTL response. The AMPHI algorithm was developed to identify helper T cell sites and consequently its relevance to CTL specificity is unknown. However, it does successfully identify the two characterized sites in influenza nucleoprotein recognized by human and murine CTL.

The fact that helper T cell immunity can be induced with short peptides as well or better than with native protein stands in sharp contrast to the situation with B cell immunity for which tertiary structure is frequently important, and indicates that peptide vaccines aimed at T cell immunity is more successful than those aimed at antibody production. In a synthetic peptide or recombinant fragment based construct, one could selectively include important helper T cell sites, in multiple copies if desired, and exclude suppressor T cell sites which can blunt the immune response. Sites associated with specific functions or possible undesirable side effects such as the CD4 binding site(s), the site(s) mediating syncytia formation, or the neuroleukin homology site, can be systematically included or excluded. For vaccines designed to induce antibodies as well as T cell immunity, incorporation of pathogen-derived T cell sites along with important B cell sites obviates the need to chemically couple small peptides to irrelevant carriers and disposes of coupling and carrier-derived problems.

Thus the T cell sites identified here are potentially important components of an effective AIDS vaccine.

The present invention includes a method of predicting which segments of a protein (along its entire sequence, if desired) are antigenic. In other words, the present invention is a method of determining which sites of an entire protein sequence are recognized by T-cells (activate or stimulate T-cells). Application of this method is limited only by knowledge of the amino acid sequences of a protein, i.e., can be applied to any protein in the protein data base of the National Biomedical Research Foundation or any protein whose sequence is subsequently published. Moreover, the analysis can be done using the amino acid sequence translated from a DNA gene sequence, without ever isolating the protein. The background experiments which made this process possible comprise, in their entirety, an examination of a number of properties to determine if a particular property(ies) is implicated in T-cell stimulation.

The following properties were determined to be fundamentally important (with a high degree of significance) in determining the potential immunogenicity of certain protein sequences:

a. the helical amphipathicity of segments along the entire sequence of a protein;

b. the conformational propensity of segments along the entire sequence of the protein;

c. the presence or absence of helix-breakers in segments along the entire sequence of the protein; and d the presence and location in the protein sequence of amino acid residues which favor T-cell recognition.

These properties, were used to develop an optimized algorithm for detecting T-cell antigenic sites (based on the amphipathic helix model) in a protein with known sequences. The optimum algorithm identifies 18 of 23 known sites (75% sensitivity), with a high degree of significance ($p < 0.001$). The success of the algorithm also shows that stable amphipathic structures such as amphipathic helices are fundamentally important in determining immunodominance. The optimized algorithm, enables the prediction of immunodominant T-cell sites on a protein. This prediction capability facilitates the rational design of synthetic vaccines, and facilitates other approaches to antigen specific T-cell recognition.

EXAMPLES

EXAMPLE 1

The AMPHI algorithm was used to examine the HTLVIII envelope protein amino acid sequence for sites with periodic variation in the hydrophobicity consistent with formation of an amphipathic helix (alpha or $3_{10}$). Overlapping blocks of 11 residues were examined and resultant parameters assigned to the middle residue. The results for the residue 100-200 and 400-500 regions encompassing the env T2 and T1 sites respectively appear on the left and right of FIG. 2. The upper panels show the amphipathic index, a measure of intensity of amphipathicity, determined at a frequency of 100° or 120° per residue. The higher of the two is shown. The lower panels display the frequency where the maximum amphipathic signal is observed. The sites were selected based on their consistently high amphipathic indices with maxima in the helical frequency range. The amino acid sequence of the indicated sites are: env T2(112-124), His-Glu-Asp-Ile-Ile-Ser-Leu-Trp-Asp-Gln-Ser-Leu-Lys: env T1(428-443), Lys-Gln-Ile-Ile-Asn-Met-Trp-Gln-Glu-Val-Gly-Lys-Ala-Met-Tyr-Ala.

EXAMPLE 2

Applying the algorithm is a major step in predicting the most probable immunodominant sites that show amphipathic helical potency. The number and length of sites along a specific protein depend on the hydrophobicity profile of that protein. There are proteins that show a high degree of amphipathic helical potency (and contain many predicted sites), while others are poor in amphathic segments. After having predicted all the possible amphipathic helical segments, the segments must be graded. The present invention prefers the use of three factors for grading purposes: a) amphipathic score (particularly useful when comparing segments of the same length); b) the rarity of proline in helices in general (except near the $NH_2$-terminus), and in most of the helical antigenic sites in particular; and c) the appearance of lysine at the carboxyl end in a large number of helical antigenic sites. It has been found that lysine as the ultimate or penultimate C-terminal residue occurs much more frequently in immunodominant sites. In short, a preferred sequence contains amphipathic segments with proline, if present, only near the N-terminus, and lysine near the C-terminus.

Another possible indicator is the presence of N-glycosylation sites--these sites are indicative of a less favorable candidate for an immunodominant site, because the T-cell epitope may be masked by the carbohydrate.

EXAMPLE 3

Using the process of this invention, the following segments were predicted to be T-cell stimulation sites:
1) segment 100-134
PheAsnMetTrpLysAsnAspMetValGluGlnMetHis-GluAspIleIleSerLeu-TrpAspGlnSerLeuLysProCys-ValLysLeuThrProLeuCysVal
2) segment 427-449
ThrLeuProCysArgIleLysGlnIleIleAsnMetTrpGln-GluValGlYLysAlaMetTyrAlaPro The numbering sequence used in this invention corresponds to Ratner et al, Nature, 313:277-284 (1985).

The underlined portion of each segment has been shown by other methods to be a T-cell stimulation site.

EXAMPLE 4

The following segments from the envelope region of the HIV genome have been predicted as candidates for T-cell stimulation sites:

| | |
|---|---|
| segment 231-250 | segment 615-652 |
| segment 307-331 | segment 659-681 |
| segment 335-357 | segment 777-808 |
| segment 553-574 | segment 827-856 |

The following segments from the gag region of the HIV genome have been predicted as candidates for T-cell stimulation sites;

| | |
|---|---|
| segment 5-22 | segment 148-162 |
| segment 52-70 | segment 284-309 |
| segment 93-110 | segment 360-376 |

The numbering sequence used in this invention corresponds to Ratner et al, Nature, 313:277-284 (1985).

The amino acid sequences for these peptides are shown in Table 3.

TABLE I

RESPONSE TO env T2 PEPTIDE IN R1O(49-474)-IMMUNE F₁ HYBRID MICE RELATIVE TO NATIVE gp120 and env T1 PEPTIDE Hybrid Mice

| Antigen | (B6 × C3H)F₁ | (A.SW × BALB/c)F₁ |
|---|---|---|
| gp120 | 69,738 | 65,949 |
|  | (1.01) | (1.07) |
| env T1 | 17,686 | 25,140 |
|  | (1.12) | (1.15) |
| env T2 | 20,703 | 23,332 |
|  | (1.18) | (1.14) |
| medium | 10,864 | 13,381 |
|  | (1.09) | (1.07) |

The experiment was performed as described in the legend to FIG. 3. [³H]-thymidine incorporation is shown for each group expressed as the geometric mean counts per minute with the standard error term for quadruplicate samples shown in parenthesis. N=8 for the medium controls. Antigen concentrations were 0.075 micromolar for gp120 and 4.8 micromolar for the env T1 and T2 peptides.

TABLE II

RESPONSE TO gp120 IN ENV T1 PEPTIDE-IMMUNE H-2 CONGENIC MICE

| | Congenic Strains | | | |
|---|---|---|---|---|
| Antigen | B1O.A(5R) | B1O.BR | B1O.S(9R) | B1O.D2 |
| PPD | 85,511 | 100,872 | 71,006 | 44,564 |
|  | (1.06) | (1.07) | (1.05) | (1.17) |
| gp120 | 45,857 | 69,456 | 68,219 | 64,858 |
|  | (1.02) | (1.05) | (1.06) | (1.10) |
| medium | 29,715 | 40,639 | 22,863 | 19,665 |
|  | (1.03) | (1.04) | (1.04) | (1.06) | the experiment was performed as described in the legend to FIG. 3. [³H]-thymidine incorporation is shown for each group expressed as the geometric means counts per minute with the standard error term for quadruplicate samples shown in parenthesis. N=8 for the medium controls. Antigen concentrations were 0.075 micromolar for gp120 and 32 micrograms per milliliter for PPD.

TABLE 3

From the env protein:

Segment 93-127
PheAsnMetTrpLysAsnAspMetValGluGlnMetHisGluAspIleIle-
SerLeuTrpAspGlnSerLeuLysProCysValLysLeuThrProLeu-
CysVal Segment 231-250
LysThrPheAsnGlyThrGlyProCysThrAsnValSerThrValGlnCys-
ThrHisGly Segment 307-331
IleArgIleGlnArgGlyProGlyArgAlaPheValThrIleGlyLysIleGly-
AsnMetArgGlnAlaHisCys Segment 335-357
ArgAlaLysTrpAsnAsnThrLeuLysGlnIleAspSerLysLeuArgGlu-
GlnPheGlyAsnAsnLys Segment 415-437
ThrLeuProCysArgIleLysGlnIleIleAsnMetTrpGlnGluValGlyLys-
AlaMetTyrAlaPro Segment 553-574
AsnAsnLeuLeuArgAlaIleGluAlaGlnGlnHisLeuLeuGlnLeuThr-
ValTrpGlyIleLys Segment 615-652
SerAsnLysSerLeuGluGlnIleTrpAsnAsnMetThrTrpMetGluTrp-
AspArgGluIleAsnAsnTyrThrSerLeuIleHisSerLeuIleGluGluSer-
GlnAsnGln Segment 659-681
GluLeuLeuGluLeuAspLysTrpAlaSerLeuTrpAsnTrpPheAsnIle-
ThrAsnTrpLeuTrpTyr Segment 777-808
IleValThrArgIleValGluLeuLeuGlyArgArgGlyTrpGluAlaLeu-
LysTyrTrpTrpAsnLeuLeuGlnTyrTrpSerGlnGluLeuLys Segment 827-856
AspArgValIleGluValValGlnGlyAlaTyrArgAlaIleArgHisIlePro-
ArgArgIleArgGlnGlyLeuGluArgIleLeuLeu From the gag protein:

Segment 5-22
AlaSerValLeuSerGlyGlyGluLeuAspArgTrpGluLysIleArg-
LeuArg

Segment 52-70
GluThrSerGluGlyCysArgGlnIleLeuGlyGlnLeuGlnProSerLeu-
GlnThr

Segment 93-110
GluIleLysAspThrLysGluAlaLeuAspLysIleGluGluGluGlnAsnLys

Segment 148-162
SerProArgThrLeuAsnAlaTrpValLysValValGluGluLys

Segment 284-309
AspIleArgGlnGlyProLysGluProPheArgAspTyrValAspArgPhe-
TyrLysThrLeuArgAlaGluGlnAla Segment 360-376
AlaArgValLeuAlaGluAlaMetSerGlnValThrAsnThrAlaThrIle

| Ala | A | Alanine | Leu | L | Leucine |
|---|---|---|---|---|---|
| Arg | R | Arginine | Lys | K | Lysine |
| Asn | N | Asparagine | Met | M | Methionine |
| Asp | D | Aspartic acid | Phe | F | Phenylalanine |
| Cys | C | Cysteine | Pro | P | Proline |
| Gln | Q | Glutamine | Ser | S | Serine |
| Glu | E | Glutamic acid | Thr | T | Threonine |
| Gly | G | Glycine | Trp | W | Tryptophan |
| His | H | Histidine | Tyr | Y | Tyrosine |
| Ile | I | Isoleucine | Val | V | Valine |

We claim:

1. A synthetic peptide having an amino acid sequence corresponding to a portion of the HIV envelope protein, where the peptide is selected from the group consisting of
   (a) HEDIISLWDQSLK,
   (b) KQIINWQEVGKAMYA,
   (c) IRIQRGPGRAFVTIGKIGNMRQAHC, and
   (d) DRVIEVVQGAYRAIRHIPRRIRQ-GLERILL.

2. The peptide of claim 1 corresponding to amino acid sequence HEDIISLWDQSLK of HIV envelope protein.

3. The peptide of claim 1 corresponding to amino acid sequence KQIINMWQEVGKAMYA of HIV envelope protein.

4. The peptide of claim 1 being IRIQRGPGRAFV-TIGKIGNMRQAHC.

5. The peptide of claim 1 being DRVIEVV-QGAYRAIRHIPRRIRQGLERILL.